United States Patent [19]

Ramey et al.

[11] 4,139,520
[45] * Feb. 13, 1979

[54] COMPOSITIONS STABILIZED WITH HINDERED PIPERIDINE CARBOXYLIC ACIDS OR METAL SALTS THEREOF

[75] Inventors: Chester E. Ramey, Spring Valley; John J. Luzzi, Carmel, both of N.Y.

[73] Assignee: Ciba-Geigy Corporation, Ardsley, N.Y.

[*] Notice: The portion of the term of this patent subsequent to Jun. 1, 1993, has been disclaimed.

[21] Appl. No.: 800,978

[22] Filed: May 26, 1977

Related U.S. Application Data

[62] Division of Ser. No. 592,006, Jun. 30, 1975, Pat. No. 4,031,095.

[51] Int. Cl.² ............................................. C08K 5/34
[52] U.S. Cl. ..................... 260/45.8 N; 260/45.85 S; 260/45.7 PH; 260/45.95 R; 260/45.8 R
[58] Field of Search ......... 260/45.8 N, 398.5, 45.85 S, 260/45.7 PH, 45.95 R, 45.8 R

[56] References Cited

U.S. PATENT DOCUMENTS

| 3,960,809 | 6/1976 | Ramey et al. | 260/45.75 N |
| 4,031,095 | 6/1977 | Ramey et al. | 260/45.75 N |
| 4,051,102 | 9/1977 | Ramey et al. | 260/45.75 N |
| 4,056,507 | 11/1977 | Ramey et al. | 260/45.8 NT |

*Primary Examiner*—V.P. Hoke
*Attorney, Agent, or Firm*—Vincent J. Cavalieri

[57] ABSTRACT

Compounds having the formula

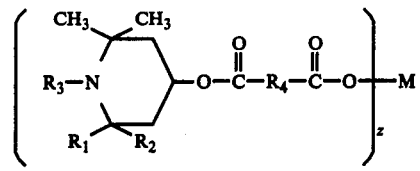

wherein
$R_1$ and $R_2$ are lower alkyl or cycloalkyl,
$R_3$ is hydrogen, alkyl, methoxyethyl, alkenyl, propargyl, benzyl or alkyl substituted benzyl,
$R_4$ is alkylene of 1 to 4 carbon atoms substituted with alkyl or alkenyl of 1 to 18 carbon atoms, alkenylene of 1 to 4 carbon atoms, cycloalkylene, cycloalkenylene, bicycloalkylene, bicycloalkenylene, or phenyllene,
M is hydrogen or a metal, and
z has a value of from 1 to 4, are good light stabilizers. The carboxylic acids are prepared for example, from 2,2,6,6-tetramethylpiperidin-4-ol and cyclohexane-1,2-dicarboxylic anhydride to give (O-mono(2,2,6,6-tetramethylpiperidin-4-ol)cyclohexane(1,2-dicarboxylate. The metal salts of the acids are readily prepared by reacting the acids or their salts with a reactive form of the metal or metal complex.

23 Claims, No Drawings

COMPOSITIONS STABILIZED WITH HINDERED PIPERIDINE CARBOXYLIC ACIDS OR METAL SALTS THEREOF

This is a divisional of application Ser. No. 592,006 filed on June 30, 1975, now U.S. Pat. No. 4,031,095.

BACKGROUND OF THE INVENTION

This invention relates to the stabilization of organic material normally tending to deteriorate. In particular, the invention relates to the protection of synthetic polymers against the harmful degradative effects, such as discoloration and embrittlement, caused by exposure to light, especially ultraviolet light.

It is known that actinic radiation, particularly in the near ultraviolet region, has a deleterious effect on both the appearance and properties of organic polymers. For example, normally colorless or light colored polyesters yellow on exposure to sunlight as do such cellulosics as cellulose acetate. Polystyrene discolors and cracks, with accompanying loss of its desirable physical properties when exposed to actinic light, while vinyl resins, such as polyvinyl chloride and polyvinyl acetate spot and degrade. The rate of air oxidation of polyolefins such as polyethylene and polypropylene is materially accelerated by ultraviolet light.

In U.S. Pat. No. 3,120,540 there is discussed the reaction of substituted 4-piperidinol compounds with acid anhydrides having formula

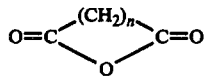

where n is 1 to 4, to yield bis(polymethyl)-4-piperidinol alkanoates. In the example of this patent the probable formation of

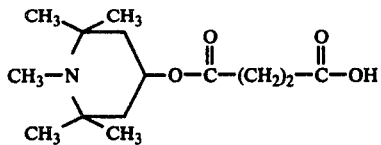

is mentioned as an intermediate in the synthesis of the bis(hydrogen sulfate)salt of bis(1,2,2,6,6-pentamehtyl-4-piperidyl)succinate. The compounds of U.S. Pat. No. 3,120,540 are taught to posess significant pharmacological activity in lowering blood pressure. We have now found that acid half esters of hindered piperidines stabilize organic substrates against the degradative effect of ultraviolet light.

DETAILED DISCLOSURE

The present invention is accordingly directed to a new class of ultraviolet light stabilizers which consists of a compound of the formula

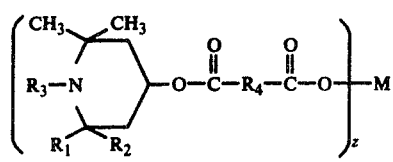

I wherein $R_1$ and $R_2$ independently of each other are straight- or branched-chain alkyl having from 1 to 6 carbon atoms, or together with the carbon to which they are bound form a cyclopentyl or cyclohexyl ring, which is unsubstituted or substituted with a methyl group, $R_3$ is hydrogen, alkyl having 1 to 12 carbon atoms, β-methoxyethyl, alkenyl having 3 to 4 carbon atoms, propargyl, benzyl or alkyl substituted benzyl, $R_4$ is straight-chain alkenylene of 2 to 4 carbon atoms, 1,2-disubstituted cycloalkylene or cycloalkenylene having 4 to 6 carbon atoms, 2,3 disubstituted bicycloalkylene or bicycloalkenylene having 7 or 8 carbon atoms or 1,2-,1,3-, or 1,4-disubstituted phenylene or straight-chain alkylene of 1 to 4 carbon atoms substituted by alkyl or alkenyl of 1 to 18 carbon atoms, provided that said straight-chain alkylene substituted has more than 8 carbon atoms, M is hydrogen or a metal selected from the group consisting of barium, nickel, manganese, calcium, copper, zinc, magnesium, sodium, potassium, cobalt, tin and dialkyl tin, and z has a value of from 1 to 4, the value of z being the same as the available valence of M.

Examples of $R_1$ and $R_2$ are methyl, ethyl, isopropyl, n-butyl and n-hexyl. Preferably, $R_1$ and $R_2$ are each lower alkyl such as a methyl group. Representative of $R_1$ and $R_2$ as cycloalkyl groups are cyclohexyl, cyclopentyl, 2-methyl, 3-methyl and 4-methylcyclohexyl, and 2-methyl and 3-methylcyclopentyl. The preferred cycloalkyl groups are cyclohexyl and 2-methylcyclohexyl. Most preferably, $R_1$ and $R_2$ are each a methyl group.

Substituent $R_3$ can be hydrogen, alkyl having 1 to 12 carbon atoms, preferably alkyl having 1 to 4 carbon atoms, methyl being particularly preferred β-methoxyethyl, alkenyl having 3 to 4 carbon atoms, preferably allyl, propargyl, benzyl or alkyl substituted benzyl. Hydrogen and methyl are particularly preferred.

Examples of $R_3$ are hydrogen, methyl, ethyl, n-propyl, isopropyl, n-butyl, isobutyl, n-hexyl, n-octyl, n-dodecyl, alkyl, α-methyallyl, propargyl, benzyl, α-methylbenzyl and α, p-dimethylbenzyl.

Examples of cyclic groups represented by $R_4$ are

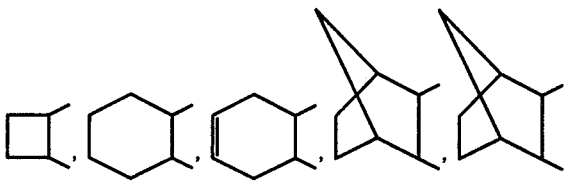

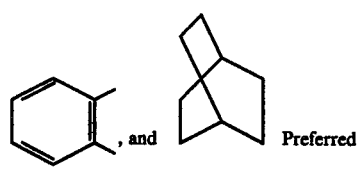, and Preferred cyclic group are 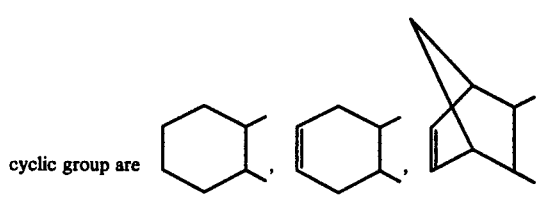

-continued and 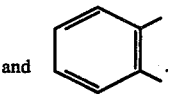

Examples of acyclic groups represented by $R_4$ are

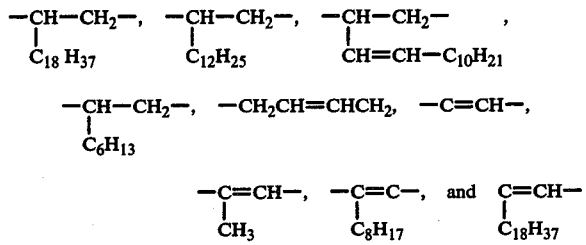

Among the substituents represented by M, hydrogen and nickel are preferred.

This invention also relates to compositions of matter which are stabilized against ultraviolet light deterioration which comprises a synthetic organic polymer normally subject to ultraviolet deterioration containing from about 0.005% to 5% by weight of the polymer of the compounds of formula I and preferably from 0.01 to 2% by weight.

The compounds as represented by formula I, can be used in combination with other light stabilizers such as 2(2-hydroxyphenyl)benzotriazoles, 2-hydroxybenzophenones, nicked complexes and benzoates.

The compounds of this invention are stabilizers or organic material normally subject to thermal, oxidative or actinic light deterioration. Materials which are thus stabilized include synthetic organic polymeric substances including homopolymers, copolymers, and mixtures thereof, such as vinyl resins formed from the polymerization of vinyl hlaides or from the copolymerization of vinyl halides with unsaturated polymerizable compounds, e.g., vinyl esters, $\alpha,\beta$-unsaturated acids, $\alpha,\beta$-unsaturated esters, $\alpha,\beta$-unsaturated ketones, $\alpha,\beta$-unsaturated aldehydes and unsaturated hydrocarbons such as butadienes and styrene; poly-$\alpha$-olefins such as high and low density polyethylene, cross-linked polyethylene, polypropylene, poly(4-methyl)pentane-1 and the like, including copolymers of $\alpha$-olefins; such as ethylene-propylene copolymers, and the like; dienes such as polybutadiene, polyisoprene, and the like, including copolymers with other monomers; polyurethanes such as are prepared from polyols and organic polyisocyanates, and polyamides such as polyhexamethylene adipamide and polycarbonates such as those prepared from bisphenol-A and phosgene; polyacetals such as polyethylene terephthalate polyacetal; polystyrene, polyethyleneoxide; polyacrylics such as polyacrylonitrile; polyphenyleneoxides such as those prepared from 2,6-dimethylphenol and the like; and copolymers such as those of polystyrene containing copolymers of butadiene and styrene and those formed by the copolymerization of acrylonitrile, butadiene and/or styrene.

Other materials which can be stabilized by the compounds of the present invention include lubricating oil of the aliphatic ester type, i.e., di(1,2-ethylene)azelate, pentaerythritol tetracaproate, and like; animal and vegetable derived oils, e.g., linseed oil, fat, tallow, lard, peanut oil, cod liver oil, castor oil, palm oil, corn oil, cottonseed oil, and the like; hydrocarbon materials such as gasoline, mineral oil, fuel oil, drying oil, cutting fluids, waxes, resins, and the like, salts of fatty acids such as soaps and the like; and alkylene glycols, e.g., $\beta$-methoxyethyleneglycol, methoxytriethyleneglycol, triethylene glycol, octaethyleneglycol, dibutyleneglycol, dipropyleneglycol and the like.

The compounds of this invention are particularly useful as UV light stabilizers, especially for the protection of polyolefins, for instance, polyethylene, polypropylene, poly(butene-1), poly(pentene-1), poly(3-methylbutene-1), poly(4-methylpentene-1), various ethylenepropylene copolymers and the like.

In general, the stabilizers of this invention are employed from about 0.01 to about 5% by weight of the stabilized composition, although this will vary with the particular substrate and application. An advantageous range is from about 0.05 to about 2% and especially 0.1 to about 1%.

For addition to polymeric substrates, the stabilizers can be blended before polymerization or after polymerization, during the usual processing operations, for example, by hot-milling, the composition then being extruded, pressed, blow molded or the like into films, fibers, filaments, hollow spheres and the like. The heat stabilizing properties of these compounds may advantageously stabilize the polymer against degradation during such processing at the high temperature generally encountered. The stabilizers can also be dissolved in suitable solvents and sprayed on the surface of films, farbics, filaments or the like to provide effective stabilization. Where the polymer is prepared from a liquid monomer as in the case of styrene, the stabilizer may be dispersed or dissolved in the monomer prior to polymerization or curing.

These compounds can also be used in combination with other additives such as antioxidants, sulfur-containing esters such as distearyl-$\beta$-thiodipropionate (DSTDP), dilauryl-$\beta$-thiodipropionate (DLTDP) in an amount of from 0.01 to 2% by weight of the organic material, and the like, pourpoint depressants, corrosion and rust inhibitors, dispersing agents, demulsifiers, antifoaming agents, fillers such as glass or other fibers, carbon black, accelerators and other chemicals used in rubber compounding, plasticizers, color stabilizers, di- and tri-alkyl- and -alkylphenyl- phosphites, as well as other phosphites, e.g., distearyl pentaeryltritol diphosphite, heat stabilizers, ultraviolet light stabilizers, antiozonants, dyes, pigments, metal chelating agents dyesites and the like. Often combinations such as these, particularly the sulfur containing esters, the phosphites and/or the ultraviolet light stabilizers will produce superior results in certain applications to those expected by the properties of the individual components.

The following formula represents co-stabilizers which are in certain instances very useful in combination with the stabilizers of this invention:

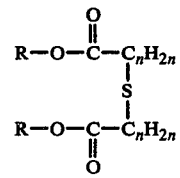

wherein R is an alkyl group having from 6 to 24 carbon atoms; and n is an integer from 1 to 6. Especially useful compounds of this are dilauryl-β-thiodipropionate and distearyl-β-thiodipropionate. The above co-stabilizers are used in the amount of from 0.01 to 2% by weight of the organic material, and preferably from 0.1 to 1%.

Although the compounds of this invention may to some degree also be effective as thermal stabilizers, if the processing of the polymer is carried out at high temperatures it is advantageous to incorporate additional antioxidants.

In most applications, it is desirable to incorporate inte the resin composition, sufficient thermal antioxidants to protect the plastic against thermal and oxidative degradation. The amount of antioxidant required will be comparable to that of the actinic stabilizer. Namely, from about 0.005% to 5% and preferably from 0.01% to 2% by weight. Representative of such antioxidants are phosphite esters, such as triphenylphosphite and dibutylphosphite and alkyl arylphosphites such as dibutylphenylphosphite, and the like.

The best results have been obtained with the preferred class of thermal antioxidants, the hindered phenols. These compounds have been found to provide the best thermal stabilization with the least discoloration in the compositions of the invention. Among these phenolic antioxidants are included the following:

di-n-octadecyl(3,5-butyl-4-hydroxy-5-methylbenzyl)-malonate
2,6-di-t-butylphenol
2,2'-methylene-bis(6-t-butyl-4-methylphenol)
2,6-di-t-butylhydroquinone
octadecyl-(3,5-di-t-butyl-4-hydroxybenzylthio)acetate
1,1,3-tris(3-t-butyl-6-methyl-4-hydroxyphenyl)butane
1,4-bis(3,5-di-t-butyl-4-hydroxybenzyl)-2,3-5,6-tetramethylbenzene
2,4-bis-(3,5-di-t-butyl-4-hydroxyphenoxy)-6-(n-octylthio)-1,3,5-triazine
2,4-bis-(4-hydroxy-3,5-di-t-butylphenoxy)-6-(n-octylthioethylthio)-1,3,5-triazine
2,4-bis-(n-octylthio)-6-(3,5-di-t-butyl-4-hydroxyanilino)-1,3,5-triazine
2,4,6-tris-(4-hydroxy-3,5-di-t-butylphenoxy)-1,3,5-triazine
n-octadecyl-β-(3,5-di-t-butyl-4-hydroxyphenyl)propionate
n-octadecyl-3,5-di-t-butyl-4-hydroxybenzoate
2-(n-octylthio)ethyl-3,5-di-t-butyl-4-hydroxybenzoate
stearamido N,N-bis[ethylene 3-(3,5-di-t-butyl-4-hydroxyphenyl)propionate]
1,2-propylene glycol bis-[3-(3,5-di-t-butyl-4-hydroxyphenyl)propionate]
pentaerythritol tetrakis-[3-(3,5-di-t-butyl-4-hydroxyphenyl)propionate]
dioctadecyl-3,5-di-t-butyl-4-hydroxybenzylphosphonate
di-n-octadecyl-1-(3,5-di-t-butyl-4-hydroxyphenyl)-ethanephosphonate The above phenolic hydrocarbon stabilizers are known and many are commercially available.

The above antioxidants have been listed only for the purpose of illustration and it is important to note that any other antioxidant can be employed with similar improved results. The above exemplified antioxidants and other related antioxidants which are incorporated herin by reference, are disclosed in greater detail in the following patents:

Netherlands Patent No. 67/1119, issued Feb. 19, 1968;
Netherlands Patent No. 68/03498 issued Sept. 18, 1968;
U.S. Pat. Nos. 3,255,191, 3,330,859, 3,644,482, 3,281,505; 3,531,483, 3,285,855; 3,364,250; 3,368,997; 3,357,944 and 3,758,549.

The compounds of this invention may be prepared by reacting a piperidinol of the formula

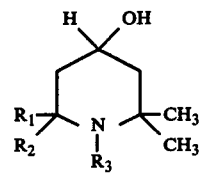

wherein $R_1$, $R_2$, and $R_3$ are as defined above as an acid anhydride of the formula

wherein $R_4$ is as defined above. In the case of 1,3 and 1,4-disubstituted phenylene, the compounds may be prepared by reacting the piperidinol II with isophthalic or terephthalic acid via usual esterification procedures.

An alternative procedure in the preparation of the compounds of this invention is the reaction of the piperidinol II with a diacid of the formula

wherein $R_4$ is as defined above.

The acids and acid anhydrides which are reacted with the compounds of formula II may be prepared by methods well known in the art.

The metal salts of the present invention can be prepared by treating the hindered piperidine carboxylic acids of formula I with a reactive form of the metal or metal complex, e.g., sodium hydroxide or the like. Alternatively, and preferably in the case of metal complexes and metals other than the alkali metals, a double decomposition is employed. Thus for example, a sodium salt of the of the present invention is treated with nickel chloride. In a similar fashion use of other halides such as manganese dicloride, barium chloride and the like results in formation of the corresponding metal derivative.

The compounds of formula II may be prepared according to procedures presented in U.S. Pat. No. 4,014,887.

The following examples, presented for illustration and not limitation, will further serve to typify the nature of the present invention.

EXAMPLE 1

O-mono(2,2,6,6-tetramethylpiperidin-4-ol) cyclohexane-1,2-dicarboxylate

A. In a 500 ml 3-necked flask equipped with a stirrer, thermometer, nitrogen inlet and Dean-Stark trap with condenser were placed 15.73 g (0.1 moles) of 2,2,6,6-tetramethylpiperidin-4-ol and 300 ml of xylene. The reaction mixture was heated briefly to reflux to remove water in the solvent, then cooled to 100° and 15.42 g (0.1 moles) of cyclohexane-1,2-dicarboxylic anhydride was added in one portion. The reaction mixture was then heated under reflux with stirring for 5 hours, then cooled to room temperature and filtered with suction. The collected solids were washed twice with hot isopropanol and dried, yielding 29.25 g of the desired product as a white powder, m.p. 231°–235°.

B. By essentially following the above procedure (A), and substituting for the cyclohexane-1,2-dicarboxylic anhydride an equivalent amount of
(a) cyclohex-4-ene-1,2-dicarboxylic anhydride
(b) bicyclo[2.2.1]hept-5-ene-2,3-dicarboxylic anhydride
(c) phthalic anhydride
there were respectively obtained the following compounds:
(a) O-mono(2,2,6,6-tetramethylpiperidin-4-ol) cyclohex-4-ene-1,2-dicarboxylate, m.p. 245°–247°
(b) O-mono(2,2,6,6-tetramethylpiperidin-4-ol) bicyclo[2.2.]hept-5-ene-2,3-dicarboxylate, m.p. 225°–229°
(c) O-mono(2,2,6,6-tetramethylpiperidin-4-ol) phthalate, m.p. 310°–325°

C. By essentially following the above procedure (A), and substituting for the reactants appropriate quantities of the following reagents:
(a) 1-n-dodecyl-2,2,6,6-tetramethyl piperidin-4-ol and cyclohex-4-ene-1,2-dicarboxylic anhydride
(b) 1-benzyl-2,2,6,6-tetramethyl piperidin-4-ol and bicyclo[2.2.1]hept-5-ene-2,3-dicarboxylic anhydride there are respectively obtained the following compounds:
(a) O-mono(1-n-dodecyl-2,2,6,6-tetramethylpiperidin-4-ol)cyclohex-4-ene-1,2-dicarboxylate
(b) O-mono(1-benzyl-2,2,6,6-tetramethylpiperidin-4-ol)bicyclo[2.2.1]hept-5-ene-2,3-dicarboxylate

EXAMPLE 2

O-mono(2,2,6,6-tetramethylpiperidin-4-ol)maleate

A. In a 300 ml 3-necked flask equipped with a stirrer, condenser with Dean-Stark trap, $N_2$ inlet, drying tube and thermometer were placed 31.82 g (0.20 moles) of 2,2,6,6-tetramethylpiperidin-4-ol and 200 ml of xylene. The reaction mixture was heated briefly to reflux, then cooled to 80° C. and 19.83 g (0.20 moles) of maleic anhydride was added. The reaction mixture was heated under reflux for 2¼ hours and allowed to cool to room temperature. The precipitate was collected by suction filtration and triturated with 400 ml of hot isopropanol. The collected solids were dried under vacuum, giving the desired material as a tan solid, m.p. 251°–253° C.

B. By essentially following the above procedure (A), and substituting for the maleic anhydride an equivalent amount of 2-dodecen-1-yl succinic anhydride there was respectively obtained O-mono(2,2,6,6-tetramethylpiperidin-4-ol)2-dodecene-1-yl succinate, m.p. 171°–174° C.

C. By essentially following the above procedure (A), and substituting for the reactants appropriate quantities of the following reagents:
(a) 1,2,2,6,6-pentamethyl piperidin-4-ol and dodecylsuccinic anhydride
(b) 1-propargyl-2,2,6,6-tetramethylpiperidin-4-ol and citraconic anhydride
there are respectively obtained the following compounds:
(a) O-mono(1,2,2,6,6-pentamethyl piperidin-4-ol) dodecyl succinate
(b) O-mono(1-prpoargyl-2,2,6,6-tetramethylpiperidin-4-ol)methylmaleate.

EXAMPLE 3

Ni(II)bis[O-mono(2,2,6,6-tetramethylpiperidin-4-ol) cyclohexane-1,2-dicarboxylate]

A. In a 500 ml 1-necked flask were placed 12.46 g (0.04 moles) of O-mono(2,2,6,6-tetramethylpiperidin-4-ol)cyclohexane-1,2-dicarboxylate and 40 ml of methanol. To the suspension was added 40.0 ml of 1.0N methanolic KOH solution and the reaction mixture was swirled until solution was obtained. The reaction mixture was then concentrated to dryness under reduced pressure and dried further under vacuum at 80°/0.1 mm for one hour. To the thus formed potassium salt was then added 100 ml of anhydrous methanol and a solution of 4.75 g (0.02 moles) of $NiCl_2.6 H_2O$ in 50 ml of methanol was added with stirring over a 10-minute period. The reaction mixture was then filtered with suction and the filtrate reduced to one-half volume under reduced pressure. To the methanolic solution was added 75 ml of ethanol, the mixture filtered with suction, and the filtrate reduced to one-half volume. The above procedure was repeated once more with ethanol, and twice more using isopropanol. After the final addition of isopropanol, the reaction mixture was filtered by suction and the filtrate concentrated under reduced pressure. The residue was dried further under vacuum at 80° C. (0.1 mm) for one hour, yielding the desired nickel salt as a green powder after grinding.

B. By following the above procedure (A) and substituting for the O-mono(2,2,6,6-tetramethylpiperidin-4-ol)cyclohexane-1,2-dicarboxylate an equivalent amount of:
(a) O-mono(2,2,6,6-tetramethylpiperidin-4-ol cyclohex-4-ene-1,2-dicarboxylate
(b) O-mono(2,2,6,6-tetramethylpiperidin-4-ol) bicyclo[2.2.1]hept-5-ene-2,3,dicarboxylate
there was respectively obtained the following materials:
(a) Ni(II) bis[O-mono(2,2,6,6-tetramethylpiperidin-4-ol)-cyclohex-4-ene-1,2-dicarboxylate], a green powder
(b) Ni(II)bis[O-mono(2,2,6,6-tetramethylpiperidin-4-ol)-bicyclo[2.2.1]hept-5-ene-2,3,dicarboxylate], a yellow green powder.

EXAMPLE 4

A. By essentially following the procedure of Example 3(A) and substituting the following metal complexes for nickel chloride
  (a) Cupric Chloride
  (b) Manganese Chloride
  (c) Cobalt(ous) Chloride
  (d) Zinc Chloride
  (e) Calcium Chloride
  (f) Magnesium Chloride
There are respectively obtained:
(a) Copper(II)bis[O-mono(2,2,6,6-tetramethylpiperidin-4-ol)cyclohexane-1,2-dicarboxylate]
(b) Manganese(II)bis[O-mono(2,2,6,6-tetramethylpiperidin-4-ol)cyclohexane-1,2-dicarboxylate]
(c) Cobaltous bis[O-mono(2,2,6,6-tetramethylpiperidin-4-ol)cyclohexane-1,2-dicarboxylate]
(d) Zinc bis[O-mono(2,2,6,6-tetramethylpiperidin-4-ol)cyclohexane-1,2-dicarboxylate]
(e) Calcium(II)bis[O-mono(2,2,6,6-tetramethylpiperidin-4-ol)cyclohexane-1,2-dicarboxylate]

B. By essentially following the procedure of Example 3(A) and substituting for the reactants appropriate quantities of the following reagents:
(a) O-mono(2,2,6,6-tetramethylpiperidin-4-ol) bicyclo[2.2.1]hept-5-ene-2,3-dicarboxylate and manganese chloride
(b) O-mono(2,2,6,6-tetramethylpiperidin-4-ol) maleate and zinc chloride
(c) O-mono(2,2,6,6-tetramethylpiperidin-4-ol) 2-dodecene-1-yl- succinate and magnesium chloride there are respectively obtained:
(a) Manganese(II)bis[O-mono(2,2,6,6-tetramethylpiperidin-4-ol)bicyclo[2.2.1]hept-5-ene-2,3-dicarboxylate]
(b) Zinc bis [O-mono(2,2,6,6-tetramethylpiperidin-4-ol)maleate]
(c) Magnesium(II)bis[O-mono(2,2,6,6-tetramethylpiperidin-4-ol)2-dodecene-1-yl succinate]

EXAMPLE 5

Ni(II)bis[O-mono(2,2,6,6-tetramethylpiperidin-4-ol)phthalate]

A. In a 500 ml 3-necked flask equipped with a stirrer, thermometer and dropping funnel were placed 15.27 g (0.05 moles) of O-mono(2,2,6,6-tetramethylpiperidin-4-ol)phthalate and 20 ml of anhydrous methanol. To the stirred suspension was added 50 ml of 1N methanolic KOH and 70 ml of methanol and the reaction mixture was stirred and heated briefly to 45° to aid solution. The reaction mixture was then cooled to room temperature and a solution of 5.94 g (0.025 moles) of $NiCl_2.6 H_2O$ in 20 ml of methanol was added over a 5-minute period, and 10 ml of methanol were used to wash the dropping funnel. The reaction mixture was allowed to stir for 10 minutes and 170 ml of isopropanol were added. After a further 45 minutes, the reaction mixture was filtered with suction and the filtrate was concentrated to dryness under reduced pressure. The residue was further dried under vacuum at 65°/0.1 mm for one hour, yielding the desired nickel salt as a green glassy poweder.

B. By essentially following the above procedure (A), and substituting the following metal complexes for nickel chloride
(a) Manganese Chloride
(b) Magnesium Chloride
(c) Zinc Chloride there are respectively obtained:
(a) Manganese(II)bis[O-mono(2,2,6,6-tetramethylpiperidin-4-ol)phthalate]
(b) Magnesium(II)bis[O-mono(2,2,6,6-tetramethylpiperidin-4-ol)phthalate]
(c) Zinc bis[O-mono(2,2,6,6-tetramethylpiperidin-4-ol)phthalate]

EXAMPLE 6

Barium bis[O-mono(2,2,6,6-tetramethylpiperidin-4-ol) cyclohexane-1,2-dicarboxylate]

In a liter 1-necked flask equipped with a magnetic stirrer were placed 15.57 g (0.05 moles) of O-mono (2,2,6,6-tetramethylpiperidine-4-ol)carboxylate and 200 ml of methanol. To the stirred suspension was added 25 ml of an IN solution of $Ba(OH)_2$ in methanol. The reaction mixture was stirred at room temperature for 15 minutes and the slurry changed character to a milky solution. The reaction mixture was evaporated to dryness under reduced pressure and the desired barium salt obtained as a colorless resin after drying under vacuum at 65%/0.1 mm.

EXAMPLE 7

Artificial Light Exposure Test

Deterioration of most polymers caused by ultraviolet light is so slow at ambient temperatures, even in the absence of stabilizers, that testing of the effects of stabilizers generally must be conducted either at higher temperatures or in an accelerated artificial light exposure device in order to yield results in a convenient period of time. The tests conducted on polymers using an artificial light exposure device is described below:

(a) Sample Preparation 5 mil Film — Unstabilized polypropylene powder (Hercules Profax 6501) is thoroughly blended with the indicated amounts of additives. The blended material is then milled on a two roll mill for 5 minutes at 182° C. The milled sheet is then compression molded at 220° C. into 5 mil thick film under a pressure of 175 psi and water cooled in the press.

(b) Testing Method

This test is conducted in a FS/BL unit, basically of the American Cyanamid design, which consists of 40 tubes of alternating fluorescent sunlamps and black lights (20 of each). The 5 mil sample film which are mounted on 3 × 2" IR card holders with 1/4 × 1" windows and are placed on a rotating drum 2 inches from the bulbs in the FS/BL unit. The time in hours is noted for the development of 0.5 carbonyl absorbance units as determined on an Infrared Spectophotometer. The development of carbonyl functional groups in the polymer is proportional to the amount of degradation caused by the ultraviolet light exposure.

The test results reported below were obtained according to the procedures described above. The amounts of the additives are expressed in weight percent based on weight of the polymer.

TABLE I

Light Stabilization Data in Polypropylene

| Additive* | Time in Hours to 0.5 Carbonyl Absorbance Units |
|---|---|
| O-mono(2,2,6,6-tetramethyl-piperidin-4-ol)cyclohexane-1,2-dicarboxylate | 1310 |
| O-mono(2,2,6,6-tetramethyl-piperidin-4-ol)cyclohex-4-ene-1,2-dicarboxylate | 570 |
| O-mono(2,2,6,6-tetramethyl-piperidin-4-ol)bicyclo[2.2.1]hept-5-ene-2,3-dicarboxylate | 1240 |
| O-mono(2,2,6,6-tetramethyl-piperidin-4-ol)phthalate | 220 |
| Ni(II)bis[O-mono(2,2,6,6-tetramethyl-piperidin-4-ol)cyclohexane-1,2-dicarboxylate] | >3010 |
| Ni(II)bis[O-mono(2,2,6,6-tetramethyl-piperidin-4-ol)cyclohex-4-ene-1,2-dicarboxylate] | 2060 |
| Ni(II)bis[O-mono(2,2,6,6-tetramethyl-piperidin-4-ol)maleate] | 990 |
| Ni(II)bis[O-mono(2,2,6,6-tetramethyl-piperidin-4-ol)phthalate] | 1210 |
| Base resin only | 200 |

TABLE II

Light Stabilization Data in Polypropylene

| Additive | Time in Hours to 0.5 Carbonyl Absorbance Units* |
|---|---|
| O-mono(2,2,6,6-tetramethyl-piperidin-4-ol)2-dodecene-1-yl succinate | 1970 |
| O-mono(2,2,6,6-tetramethyl-piperidin-4-ol)maleate | 2510 |
| Ni(II)bis[O-mono(2,2,6,6-tetramethyl-piperidin-4-ol)-2-dodecene-1-yl succinate] | 3420 |
| Ni(II)bis[O-mono(2,2,6,6-tetramethyl-piperidin-4-ol)-bicyclo[2.2.1]hept 5-ene-2,3-dicarboxylate] | >1520 |
| Base resin only | 420 |

*The formulation contains 0.5% additive and base resin containing 0.2% antioxidant dioctadecyl 3,5-di-t-butyl-4-hydroxybenzylphosphonate.

Other hindered phenolic antioxidants may be used in place of di-octadecyl(3,5-di-t-butyl-4-hydroxybenzyl)-phosphonate in the above mentioned compositions, for example, di-n-octadecyl α-(3-t-butyl-4-hydroxy-4-methylbenzyl)malonate, 2,4-bis(n-octylthio)-6-(3,4-di-t-butyl-4-hydroxyaniline)-1,3,5-triazine, octadecyl 3-(3',5'-di-t-butyl-4'-hydroxyphenyl)propionate, pentaerythritol-tetrakis[3-(3,5-di-t-butyl-4-hydroxyphenyl)]-propionate, tris-(3,5,di-t-butyl-4-hydroxybenzyl-)isocyanurate, 2,6-di-tert-butyl-4-methylphenol, N,N,N-tris-(3,5-di-tert-butyl-4-hydroxybenzyl-)isocyanurate, and 2,4,6-tris(3,5-di-tert-butyl-4-hydroxybenzyl)-1,3,5-trimethylbenzyl.

The following UV absorbers are included in the formulation at 0.01 to 2%:
(a) 2(2'-hydroxy-3',5'-di-t-butylphenyl)-5-chlorobenzotriazole
(b) 2-hydroxy-4-methoxy-5-sulfobenzophenone trihydrate
(c) 2-hydroxy-4-n-octoxybenzophenone
(d) [2,2'-thiobis(4-t-octylphenolate)]-n-butylamine nickel II
(e) p-octylphenyl salicylate
(f) 2,2'-dihydroxy-4,4'-dimethoxybenzophenone
(g) 2(2'-hydroxy-5'-methylphenyl)-benzotriazole.

EXAMPLE 8

High impact polystyrene resin containing elastomer (i.e., butadiene-styrene) is stabilized against loss of elongation properties due to exposure to ultraviolet light by incorporation of 0.2% by weight of O-mono(2,2,6,6-tetramethylpiperidin-4-ol)cyclohexane-1,2-dicarboxylate.

The unstabilized resin is dissolved in chloroform and the stabilizer then added, after which the mixture is cast on a glass plate and the solvent evaporated to yield a uniform film which, upon drying, is removed and cut up, and then pressed for 7 minutes at a temperature of 163° C. and a pressure of 2,000 pounds per square inch into sheet of uniform thickness (25 mil). The sheets are then cut into strips approximately 4 × 0.5 inches. A portion of these strips is then measured for percent of elongation in the Instron Tensile Testing Apparatus (Instron Engineering Corporation, Quincy, Massachusetts). The remaining portions of the strips are placed in an FS/BL chamber according to Example 6(B) except that the sameple are mounted and white cardboard stock and the time to 50% reduction in elongation is measured. The stabilized polystyrene resin retains its elongation property longer than the unstabilized resin.

EXAMPLE 9

Unstabilized linear polyethylene is solvent blended in methylene chloride with 0.5% by weight of the substrate of the nickel complex of O-mono(2,2,6,6-tetramethylpiperidin-4-ol)maleate and then vacuum dried. The resin is then extrusion compounded on a 1 inch 24/1=L/D extruder, melt temperature 450° F. (232° C.) and pressed for 7 minutes at a temperature of 163° C. and a pressure of 2,000 psi into a sheet of uniform thickness of 100 mil. The sheets are then cut into plaques of 2 inch × 2 inch. The plaques are then exposed in an FS/BL exposure device and color measurements made periodically using a Hunter Color Difference Meter Model D25. Polyethylene stabilized with the above compound is found to be much more stable than the unstabilized polyethylene or the polyethylene stabilized only with an antioxidant.

EXAMPLE 10

A quantity of SBR emulsion containing 100 g of rubber (500 ml of 20% SBR obtained from Texas U.S., Synpol 1500) previously stored under nitrogen, is placed in a beaker and stirred vigorously. The pH of the emulsion is adjusted to 10.5 with a 0.5N NaOH solution.

To the emulsion is added 50 ml of 25% NACl solution. A 6% NaCl solution adjusted with hydrochloric acid to a pH 1.5 is added in a thin stream with vigorous stirring. When pH 6.5 is reached, the rubber begins to coagulate and the addition is slowed down in order to maintain uniform agitation. The addition of the acidic 6% NaCl solution is terminated when a pH 3.5 is reached. The coagulated crumb-rubber slurry at pH 3.5 is stirred for one-half hour.

The coagulated rubber is isolated by filtration through cheese cloth, and rinsed with distilled water. After three subsequent washings with fresh distilled water, the coagulated rubber is dried, first at 25 mm Hg and finally to constant weight under high vacuum (>1 mm) at 40°–45° C.

The dried rubber (25 g) is heated under nitrogen at 125° C. in a Brabender mixer and to this is added with mixing 0.25 g (0.5%) of O-mono(2,2,6,6-tetramethylpiperidin-4-ol)cyclohex-4-ene-1,2-dicarboxylate, is mixed for 5 minutes after which it is cooled and compression molded at 125° C. into 5 × 0.025" plaques.

The plaques are exposed to an Xenon Arc weatherometer and the color measurement (L-b) is made after 45, 125 and 290 hours. The samples stabilized with the above compound are found to be much more light stable than the unstabilized samples.

EXAMPLE 11

The 50 g of polyacetal resin containing 0.1% of an acid scavenger, dicyandiamide, is added 0.2% by weight of Ni(II)bis[O-mono(2,2,6,6-tetramethylpiperidin-4-ol)-2-dodecen-1-yl succinate] and milled for 7 minutes at 200° C. in a Brabender Plasti-recorder. The milled formulation is subsequently pressed into a 40 mil sheet at 215° C. at 350 psi for 90 seconds then cooled quickly in a cold press at 350 psi. The stabilized sheets are then remolded for 2 minutes at contact pressure and for 3 minutes at 300 psi at 215° C. to give plaques 1½ inch × 2½ inch × 125 mil. Thereafter, the testing procedure of Example 8 is followed to determine the light stability of the samples. The stabilized samples are found to be much more stable than the unstabilized samples.

EXAMPLE 12

Unstabilized thoroughly dried polyethylene terphthalate chips are dry blended with 1.0% of O-mono 2(2,2,6,6-tetramethylpiperidin-4-ol)2-dodecene-1-ly succinate. 60/10 denier multifilament is melt spun at a melt temperature of 290° C. The oriented fiber is wound on white cards and exposed in an Xenon Arc Fadeometer. Color measurements are made periodically with a Hunter Color Difference Meter Model D25. The stabilized samples are found to be much more light stable than the unstabilized samples.

EXAMPLE 13

(a) A composition comprising acrylonitrile-butadiene-styrene terpolymer and 1% by weight of Ni(II) bis[O-mono(2,2,6,6-tetramethylpiperidin-4-ol)maleate] resists embrittlement due to exposure to ultraviolet light longer than one which does not contain the stabilizer.

(b) A composition comprising polyurethane prepared from toluene diisocyanate and alkylene polyols and 1.0% by weight of O-mono(2,2,6,6-tetramethylpiperidin-4-ol)cyclohexane-1,2-dicarboxylate is more stable to sunlight, fluorescent sunlamps, black lights and fluorescent lights than the unformulated polyurethane.

(c) A composition comprising a polycarbonate prepared from bisphenol-A and phosgene and 1% by weight of O-mono(2,2,6,6-tetramethylpiperidin-4-ol)bicyclo[2.2.1] hept-5-ene-2,3-dicarboxylate resists discoloration due to exposure to ultraviolet light longer than one which does not contain the stabilizer.

(d) A composition comprising polymethylmethacrylate and 0.25% by weight of Ni(II)bis[O-mono(2,2,6,6-tetramethylpiperidin-4-ol)cyclohexane-1,2-dicarboxylate] resists discoloration due to exposure to ultraviolet light longer than one which does not contain the stabilizer.

EXAMPLE 14

(a) A stabilized polyamide (nylon 6,6) is prepared by incorporating therein 0.1% of Ni(II)bis[O-mono (2,2,6,6-tetramethylpiperidin-4-ol)bicyclo[2.2.1]hept-5-ene-2,3-dicarboxylate]. The light stability of the stabilized composition is superior to that of an unstabilized polyamide.

(b) A stabilized polyphenylene oxide polymer (prepared by polymerizing 2,6-dimethylphenol is prepared by incorporating therein 0.5% by weight of Ni(II)bis[O-mono (2,2,6,6-tetramethylpiperidin-4-ol)cyclohex-4-ene-1,2-docarboxylate]. The stabilized compositions resists embrittlement due to exposure to ultraviolet light longer than one which does not contain the stabilizer.

(c) A stabilized crystalline polystyrene is prepared by incorporating therein 0.1% weight of Ni(II)bis [O-mono(2,2,6,6-tetramethylpiperidin-4-ol)cyclohex-4-ene-1,2-dicarboxylate]. The stabilized composition resists embrittlement due to exposure to ultraviolet light longer than one which does not contain the stabilizer.

Antioxidants may also be incorporated into each of the above mentioned compositions, for example, di-n-octadecyl-α,α'-bis(3-butyl-4-hydroxy-5-methylbenzyl)-malonate 2,4-bis(4-hydroxy-3,5-di-t-butylphenoxy)-6-(n-octylthioethylthio)-1,3,5-triazine, 2,4-bis(3,5-di-t-butyl-hydroxyphenoxy)-6-(n-octylthio-1,3,5-triazine di-n-octadecyl 3(3',5'-di-t-butyl-4-hydroxyphenyl)propionate, respectively.

The invention encompasses compounds having the formula

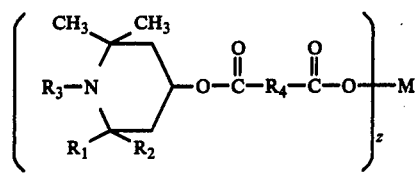

In the above structure M is hydrogen or a metal and may also be $M'(R)_n$ where R represents water, alcohols, glycols, diols, triols, tetraols, pentols, hexitols as well as ammonia, amines and amino alcohols. $M^1$ is metal. In the case of $M'_{,z}$ represents the primary value and n represents the coordination number of the metals.

The compounds wherein M is $M'(R)_n$ may be prepared by mixing equimolar ratios of the compounds containing M and the co-ligand R in an appropriate solvent, refluxing, and subsequently evaporating to dryness. More specifically, when M is Nickel R is n-butylamine the compound may be suspended in isopropanol, the n-butylamine added, and the mixture refluxed until solution is achieved, then evaporated to dryness.

What is claimed is:

1. A composition of matter stabilized against ultraviolet deterioration which comprises a synthetic organic polymer normally subject to ultraviolet deterioration containing from (a) 0.005% to 5% of a stabilizing compound of the formula

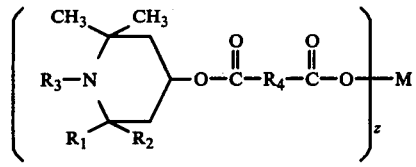

$R_1$ and $R_2$ independently of each other are straight- or branched-chain alkyl having from 1 to 6 carbon atoms, or together with the carbon to which they are bound form a cyclopentyl or cyclohexyl ring, which is unsubstituted or substituted with a methyl group, $R_3$ is hydrogen, alkyl having 1 to 12 carbon atoms, β-methoxyethyl, alkenyl having 3 to 4 carbon atoms propargyl, benzyl, or alkyl substituted benzyl, $R_4$ is straight-chain alkenylene of 2 to 4 carbon atoms, 1,2-disubstituted cycloalkylene or cycloalkenylene having 4 to 6 carbon atoms, 2,3-disubstituted bicycloalkylene or bicycloalkenylene having 7 to 8 carbon atoms or 1,2-, 1,3- or 1,4-disubstituted phenylene, or a straight-chain alkylene of 1 to 4 carbon atoms substituted by alkyl or alkenyl of 1 to 18 carbon atoms, provided that the straight-chain alkylene substituted by alkyl has more than 8 carbon atoms, M is hydrogen or a metal selected from the group consisting of barium, nickel, manganese, calcium, copper, zinc, magnesium, sodium, potassium, cobalt, tin and dialkyl tin, and z has a value of from 1 to 4, the value of z being the same as the available valence of M, (b) 0 to 5% of a phenolic antioxidant,
(c) 0 to 5% of a thio co-stabilizer, and
(d) 0 to 5% of a U.V. absorber.

2. A composition of claim 1 wherein $R_1$ and $R_2$ in the stabilizer are each methyl.

3. A composition of claim 2 wherein M in the stabilizer is selected from hydrogen or nickel.

4. A composition of claim 1 wherein the stabilizer is Ni(II)bis[O-mono(2,2,6,6-tetramethylpiperidin-4-ol)cyclohexane-1,2-dicarboxylate].

5. A composition of claim 1 wherein the stabilizer is Ni(II)bis[O-mono(2,2,6,6-tetramethylpiperidin-4-ol)cyclohex-4-ene-1,2-dicarboxylate].

6. A composition of claim 1 wherein the stabilizer is Ni(II)bis[O-mono(2,2,6,6-tetramethylpiperidin-4-ol)-dodecene-1-yl-succinate].

7. A composition of claim 1 wherein the stabilizer is Ni(II)bis[O-mono(2,2,6,6-tetramethylpiperidin-4-ol)bicyclo[2.2.1]hept-5-ene-2,3-dicarboxylate].

8. The composition of claim 1 wherein the stabilizer is Ni(II)bis[O-mono(2,2,6,6-tetramethylpiperidin-4-ol)phthalate].

9. A composition of claim 1 wherein the stabilizer is Ni(II)bis[O-mono(2,2,6,6-tetramethylpiperidin-4-ol)maleate].

10. A composition of claim 1 wherein $R_4$ of the stabilizer is 1,2-disubstituted cycloalkylene or cycloalkenylene having 4 to 6 carbon atoms.

11. A composition of claim 1 wherein $R_4$ of the stabilizer is 2,3-disubstituted dicycloalkylene or bicycloalkenylene having 7 to 8 carbon atoms.

12. A composition of claim 1 wherein $R_4$ of the stabilizer is 1,2-, 1,3- or 1,4-disubstituted phenylene.

13. A composition of claim 1 wherein $R_4$ of the stabilizer is straight-chain alkenylene of 2 to 4 carbon atoms.

14. A composition of claim 1 wherein $R_4$ of the stabilizer is straight-chain alkylene of 1 to 4 carbon atoms substituted by alkyl or alkenyl of 1 to 18 carbon atoms.

15. A composition of claim 1 wherein the stabilizer O-mono-(2,2,6,6-tetramethylpiperidin-4-ol)cyclohexane-1,2-dicarboxylate.

16. A composition of claim 1 wherein the stabilizer is O-mono(2,2,6,6-tetramethylpiperidin-4-ol)bicyclo[2.2.1]hept-5-ene-2,3-dicarboxylate.

17. A composition of claim 1 wherein the stabilizer is O-mono(2,2,6,6-tetramethylpiperidin-4-ol)2-dodecene-1-yl succinate.

18. A composition of claim 1 wherein the stabilizer is O-mono(2,2,6,6-tetramethylpiperidin-4-ol)maleate.

19. A composition of claim 1 wherein the stabilizer is O-mono(2,2,6,6-tetramethylpiperidin-4-ol)cyclohex-4-ene-1,2-dicarboxylate.

20. A composition of claim 1 wherein the stabilizer is O-mono(2,2,6,6-tetramethylpiperidin-4-ol)phthalate.

21. A composition of claim 1 wherein the organic material is a polyolefin.

22. A composition of claim 21 wherein the polyolefin in polypropylene.

23. A composition of matter stabilized against ultraviolet deterioration which comprises a synthetic organic polymer normally subject to ultraviolet deterioration containing from
   (a) 0.005% to 5% of a stabilizing compound having the formula $$\left\{ \begin{array}{c} CH_3 \quad CH_3 \\ R_3-N \\ R_1 \quad R_2 \end{array} \right. -O-\overset{O}{\overset{\|}{C}}-R_4-\overset{O}{\overset{\|}{C}}-O \left. \right\}_z M$$

$R_1$ and $R_2$ independently of each other are straight- or branched-chain alkyl having from 1 to 6 carbon atoms, or together with the carbon to which they are bound form a cyclopentyl or cyclohexyl ring, which is unsubstituted or substituted with a methyl group, $R_3$ is hydrogen, alkyl having 1 to 12 carbon atoms, β-methoxyethyl, alkenyl having 3 to 4 carbon atoms propargyl, benzyl, or alkyl substituted benzyl, $R_4$ is straight-chain alkenylene of 2 to 4 carbon atoms, 1,2-disubstituted cycloalkylene or cycloalkenylene having 4 to 6 carbon atoms, 2,3-disubstituted bicycloalkylene or bicycloalkenylene having 7 to 8 carbon atoms or 1,2-, 1,3- or 1,4-disubstituted phenylene, or a straight-chain alkylene of 1 to 4 carbon atoms substituted by alkyl or alkenyl of 1 to 18 carbon atoms, provided that the straight-chain alkylene substituted by alkyl has more than 8 carbon atoms, M is hydrogen or a metal selected from the group consisting of barium, nickel, manganese, calcium, copper, zinc, magnesium, sodium, potassium, cobalt, tin and dialkyl tin, and Z has a value of from 1 to 4, the value of Z being the same as the available valence of M, (b) 0 to 5% of a phenolic antioxidant,
(c) 0 to 5% of a phosphite co-stabilizer and
(d) 0 to 5% of a UV absorber.

* * * * *